United States Patent
Niklaus et al.

(10) Patent No.: US 8,114,056 B2
(45) Date of Patent: Feb. 14, 2012

(54) DEVICE FOR PREVENTING A FREE CATHETER FLOW

(75) Inventors: Hanspeter Niklaus, Riken (CH); Roger Haenggi, Nunningen (CH)

(73) Assignee: Roche Diagnostics International AG, Steinhausen (CH)

(*) Notice: Subject to any disclaimer, the term of this patent is extended or adjusted under 35 U.S.C. 154(b) by 0 days.

(21) Appl. No.: 12/644,446

(22) Filed: Dec. 22, 2009

(65) Prior Publication Data

US 2010/0185151 A1    Jul. 22, 2010

Related U.S. Application Data

(63) Continuation of application No. PCT/EP2008/004281, filed on May 29, 2008.

(30) Foreign Application Priority Data

Jun. 29, 2007  (EP) .................................. 07111423

(51) Int. Cl.
*A61M 5/00* (2006.01)
(52) U.S. Cl. ........................................ 604/250
(58) Field of Classification Search ............. 604/246, 604/247, 250, 256
See application file for complete search history.

(56) References Cited

U.S. PATENT DOCUMENTS

| | | | |
|---|---|---|---|
| 3,103,335 A | | 9/1963 | Martinez |
| 4,515,589 A | | 5/1985 | Austin et al. |
| 4,767,289 A | * | 8/1988 | Parrott et al. .......... 417/477.12 |
| 5,186,431 A | * | 2/1993 | Tamari ................. 251/5 |
| 5,250,034 A | * | 10/1993 | Appling et al. .......... 604/164.02 |
| 5,396,925 A | * | 3/1995 | Poli .................. 137/493 |
| 5,522,806 A | * | 6/1996 | Schonbachler et al. ....... 604/250 |
| 5,814,004 A | * | 9/1998 | Tamari ............... 604/6.1 |
| 6,039,078 A | * | 3/2000 | Tamari .............. 138/30 |
| 6,454,742 B1 | | 9/2002 | Noecker et al. |
| 6,554,589 B2 | * | 4/2003 | Grapes ................ 417/477.12 |
| 2004/0087911 A1 | | 5/2004 | Feliciano |

FOREIGN PATENT DOCUMENTS

| | | |
|---|---|---|
| EP | 0273714 | 7/1988 |
| EP | 0 882 466 A2 | 12/1998 |
| EP | 1466646 | 10/2004 |
| WO | 95/16480 A1 | 6/1995 |
| WO | 97/02059 A1 | 1/1997 |

OTHER PUBLICATIONS

International Search Report, May 29, 2008 for Application No. PCT/EP2008/004281.

* cited by examiner

*Primary Examiner* — Nicholas Lucchesi
*Assistant Examiner* — Aarti B Berdichevsky
(74) *Attorney, Agent, or Firm* — Dinsmore & Shohl LLP

(57) ABSTRACT

A catheter for connecting an administering device to an administering needle, the catheter including a catheter wall, a flow region limited by the catheter wall, and at least one catheter portion at which at least one partial piece of the catheter wall abuts at least one other partial piece of the catheter wall to releasably block or obstruct the flow of a medium through the catheter, wherein the flow is unblocked or opened when the medium exhibits a pressure above a predetermined blocking pressure.

19 Claims, 4 Drawing Sheets

DEVICE FOR PREVENTING A FREE CATHETER FLOW

CROSS-REFERENCE TO RELATED APPLICATIONS

This application is a continuation of International Patent Application No. PCT/EP2008/004281 filed on May 29, 2008, which claims priority to European Application No. 07 111 423.5, filed on Jun. 29, 2007, the entire contents of both of which are incorporated herein by reference.

BACKGROUND

The present invention relates to devices for delivering, injecting, infusing, administering or dispensing a substance, and to methods of making and using such devices. More particularly, it relates to a device for preventing a flow through a catheter, and more particularly to a catheter formed such that a flow of a fluid through the catheter due to a hydrostatic pressure of the fluid or liquid flowing through, channeled in or conducted through the catheter is blocked or prevented. The present invention also relates to a system comprising such a catheter and an administering device, e.g. an infusion pump.

Known infusion systems store a drug to be administered in a container, usually an ampoule, in which a carrier fluid with the drug dissolved in it—referred to in the following simply as the drug fluid—is situated between a movable stopper and a container outlet. One end, which may be thought of as the rear end, of a catheter is connected to the container outlet. A needle, which is introduced into the human or animal body to administer the drug fluid, is placed on the other, front, end of the catheter and in most cases remains there for an administering period which is often several days, wherein if the container with the drug fluid is situated at a greater height than the front end of the catheter and/or the needle, there exists the danger, if the difference in height between the container and the front end of the catheter is large enough, of the container gradually emptying itself due to the force of the column of fluid.

In insulin therapy using portable infusion apparatus, for example pump apparatus, the catheters used can exhibit lengths of more than 1 m. If the apparatus, including the container, is arranged vertically above the user, for example at night or when showering, a hydrostatic ground pressure of about 0.1 bar is generated, if no other effects—for example friction losses, discharge effects or capillary action—are taken into account in addition to the purely static pressure due to the inherent weight of the drug fluid, and if the density of water is assumed for the drug fluid.

To prevent any undesirable discharge due to the pressure of the column of fluid, the wall friction between the stopper, which is accommodated in the container such that it can slide freely, and the container wall could be increased; however, this would incur other disadvantages. Another solution would be to fix the stopper to the driven member of an infusion pump, such that the stopper prevents the surface of the fluid from dropping in the container and so prevents it from emptying itself. Known systems involving screwing the stopper to the driven member. This, however, increases the cost of the apparatus. Also, this solution cannot be used with prefabricated ampoules, since the stopper is not prepared for a screw connection.

International application WO 97/02059 relates to an infusion pump comprising a pump casing and a safety valve which is intended to prevent delivery of the drug from being caused by gravity alone. The connecting casing of the pump is detachably fastened to the pump casing. Also, its upstream end is connected to a sack-like drug reservoir via a catheter and an inlet connector.

International application WO 95/16480 discloses an infusion device comprising a drug container, a catheter leading away from it, a clamp arranged on the catheter, a pump connected to the catheter, another catheter leading from the pump to the patient, and a safety valve arranged in said other catheter. By means of the clamp for the first catheter and the safety valve, the intention is to prevent the drug fluid from being undesirably conveyed due to gravity.

EP 0 882 466 A2 discloses a device for administering, in particular infusing, a drug fluid in doses, comprising a container from which the drug fluid is displaced in doses through an outlet when a stopper is advanced, to administer it, and comprising a catheter which is connected to the container at the outlet, wherein the front end of said catheter facing away from the outlet is or can be connected to an administering needle, wherein a valve is arranged between the outlet and the administering needle in a flow cross-section of the drug fluid, and the valve only allows a flow toward the front end of the catheter when the fluid pressure acting in this direction is greater than a pressure bearing on the valve as a result of the inherent weight of a column of fluid in the device, to prevent the container from emptying itself.

SUMMARY

An object of the present invention to provide a catheter and a system comprising the catheter and an administering device which prevent a drug fluid or substance to be dispensed through the catheter from being dispensed or discharged in an uncontrolled manner.

In one embodiment, the present invention comprises a catheter for connecting an administering device to an administering needle, the catheter including a catheter wall, a flow region limited by the catheter wall, and at least one catheter portion at which at least one partial piece of the catheter wall abuts at least one other partial piece of the catheter wall to releasably block or obstruct the flow of a medium through the catheter, wherein the flow is unblocked or opened when the medium exhibits a pressure above a predetermined blocking pressure.

In one embodiment, a catheter in accordance with the present invention for connecting an administering device, for example an infusion pump which is known in its own right, to an administering needle which can be included in a so-called infusion set, comprises a catheter wall which is provided as a continuous one-part wall of a tubular or flexible tubular catheter made from an elastic material. The inside of the catheter wall (or walls) limits or defines the flow region of the catheter, through which a drug fluid or substance, dispensed from an infusion pump, is conveyed to an administering point and to an administering needle. In one embodiment, in accordance with the present invention, the catheter comprises at least one catheter portion at which at least one partial piece of the inner wall of the catheter abuts at least one other partial piece of the inner wall of the catheter, to automatically block or obstruct the flow through the catheter, wherein the flow is re-enabled and the catheter opened when the fluid being guided in the catheter exhibits a pressure above a predetermined minimum pressure of, for example, more than 0.1 bar or more than 0.2 bar.

Providing a catheter portion comprising an inner wall of the catheter which, in its normal state without the application of a predeterminable minimum pressure of the fluid being guided by the catheter, is automatically deformed—for example by correspondingly shaping the catheter wall and/or using specific, for example elastic, materials or by applying an external force such as for example attaching one or more clamping pieces—such that a flow through the catheter is only possible once a predeterminable minimum pressure of, for example, more than 0.1 bar is exceeded, has the advantage that additional valves do not have to be provided at the end of the catheter or in the catheter to control and/or prevent a free flow. A self-blocking catheter in accordance with the present invention can thus be designed very simply and also prevents incorrect use, since additional valves do not have to be connected and therefore also cannot be forgotten when using the catheter.

In some preferred embodiments, a catheter in accordance with the present invention may advantageously comprise two or more catheter portions which are, for example, spaced apart from each other in the longitudinal direction, i.e. along a length of, and/or in flow direction of the catheter, to form two or more zones to prevent a free flow through the catheter when a pressure below the predetermined minimum pressure is applied. For example, two or more zones can be formed in immediate succession, within which the inner walls or surface(s) of the catheter abut each other, wherein preventing a free flow at a pressure below the predeterminable minimum pressure can be realized by an individual zone, e.g. by the inner walls of the catheter abutting each other, or by automatic sealing within an individual region or zone, or also by a number of successively arranged zones co-operating, in which the catheter walls abut each other, spaced apart from each other in the longitudinal direction of the catheter, at a number of portions and thus form a number of blocking or securing elements along the length of the catheter.

In some embodiments, the minimum pressure which has to be applied to re-open the self-blocking or self-sealing on the catheter is around at least 0.1 bar and, in some preferred embodiments, above 0.1 bar, i.e. in the range above 0.15 bar or 0.2 bar or above 0.3 bar or 0.7 bar.

When the ampoule is biased, i.e. a minimum impact force is applied to the stopper, it may be that the fluid pressure at the outlet region of the ampoule is around a higher pressure of, for example, 0.5 bar. Accordingly, in some embodiments, the opening pressure of the catheter should be around this higher pressure, plus a safety pressure of, for example, 0.1 bar or 0.2 bar.

In some preferred embodiments, to obstruct administering the drug in doses as little as possible, but still securely prevent discharge, the catheter is configured such that it only allows the flow toward the front end of the catheter when the fluid pressure in this direction (the flow direction) exceeds the maximum possible pressure of the column of fluid, in some embodiments, multiplied by a safety factor. Since, in the present case, the valve is being used in the medicinal field, the safety factor may correspond to the value 3. For a maximum catheter length of about 1 m and a negligible column of fluid in the container, the maximum fluid pressure at the free end of the catheter measures about 0.1 bar, such that in this case, the catheter is configured such that it only opens when the fluid pressure exceeds 0.3 bar. These are also the dimensions for an exemplary preferred use in a portable infusion pump.

In some preferred embodiments, the catheter is self-closing or self-blocking below the aforementioned blocking pressure or minimum pressure and can thus effectively prevent a substance or drug fluid from unintentionally flowing through it due to the pressure of the column of fluid within the catheter.

In some preferred embodiments, a catheter in accordance with the present invention comprises regions or portions in which the walls of the flexible tube are biased against each other. This can, for example, be achieved by only one partial piece being biased toward another, for example opposing inner wall of the catheter in the circumferential direction of the catheter, or by two regions of the catheter wall which oppose each other being biased toward each other, to abut each other when there is a lack of pressure in the medium being guided in the catheter, such that the flow is blocked below the mentioned minimum pressure which enables a flow. A partial piece of the catheter or a region of the catheter wall can, for example, be biased by using an elastic material which is provided on or in the catheter or as a part of the catheter wall, such that one or more catheter walls are biased in a direction which reduce and, in some embodiments, completely seal the flow region, i.e. an opening within the catheter.

Alternatively or additionally, an external element, for example a clip or clamping device, which is formed as a suitably-shaped, e.g. U-shaped, spring element can generate an external force which acts on the outer wall or walls of the catheter, to press together the catheter between or by the clip element or spring element. When the predeterminable minimum pressure is applied, for example generated by an infusion pump, a fluid passing through the catheter can press the external element apart far enough to enable a flow through the catheter, which is limited in accordance with the pressure being applied or which is unobstructed.

In some embodiments, the catheter can also be reshaped by a production process or by an external element, such as a clamping element, such that the catheter is not annular in cross-section like known catheters but rather exhibits a different shape which is advantageous for blocking a flow, for example, in some embodiments, a catheter in accordance with the present invention may have the shape of a flat flexible tube in which the wall halves abut each other and can thus prevent a flow at a low pressure.

Furthermore, in some embodiments, it is also possible for the catheter to be embodied so as to be bent or sharply bent and for this bent or sharply bent shape to be realized either by the catheter materials, by catheter geometry used, and/or by an external element such as a clamping piece which holds the catheter in a bent or sharply bent shape.

In accordance with another aspect of the present invention, the invention comprises a system comprising a catheter such as has been described above and an administering device, e.g. an infusion pump, for administering a drug fluid in doses, wherein the drug fluid is contained in a container from which it is displaced, to be administered, in doses by advancing a stopper which is movably accommodated in the container toward a container outlet. The rear end of a catheter such as has been described above can be connected directly to the outlet of the container, where an outlet piece and/or outlet support for connecting a catheter is provided. The catheter is usually a flexible tubular catheter. It would, however, be equally possible to use a rigid catheter comprising elastic partial pieces. The front, free end of the catheter is or can be connected to a needle for administering the drug. "Administering" is understood to mean both infusing and injecting and/or a combination of the two types of administering. Thus, in some embodiments, the present invention is intended to be used in infusion devices and/or infusion apparatus, which may be portable pump apparatus for insulin treatment.

In some preferred embodiments, the self-blocking element or partial piece of the catheter is arranged between the container outlet and the needle for administering the drug, in a flow cross-section of the drug fluid. The catheter is dimensioned such that, to prevent it from emptying itself, it only allows a flow toward the front end of the catheter when the fluid pressure acting in this direction is greater than a pressure bearing on the self-blocking portion as a result of the inherent weight of the column of fluid in the device. If the device is a mass-produced device, for which a whole range of catheters having different lengths are available, then the self-blocking portion is dimensioned for using the longest catheter, i.e. for the maximum possible column of fluid.

Although the self-blocking portion or the self-blocking partial regions of the catheter can in principle be placed at any point between the container outlet and/or infusion pump and the administering needle, in some preferred embodiments the portion or region is arranged as near as possible to the outlet of the container or as near as possible to the infusion pump.

In accordance with another aspect of the present invention, it comprises a method for preventing a free flow through a catheter, wherein at least a partial region of the catheter or the catheter wall prevents the flow of a medium below a predetermined minimum pressure, and wherein the catheter is pressed open to enable the flow when the medium exceeds the minimum pressure.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1A:
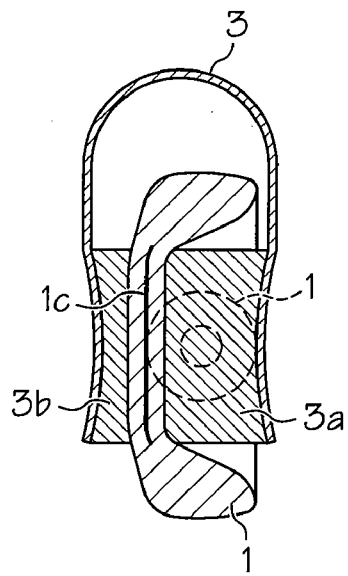
FIG. 1A is a sectional view along the line A-A in FIG. 1.
Figure 1B:
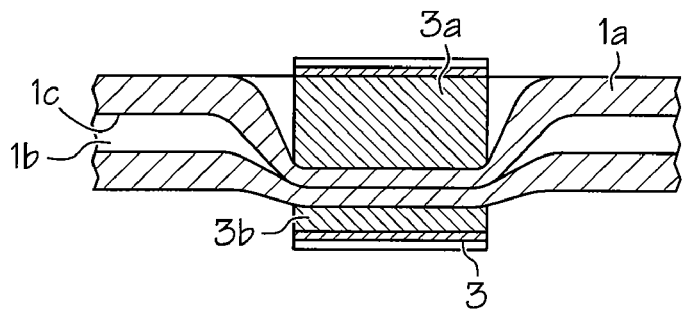
FIG. 1B is a sectional view along the line B-B in FIG. 1.
Figure 1:
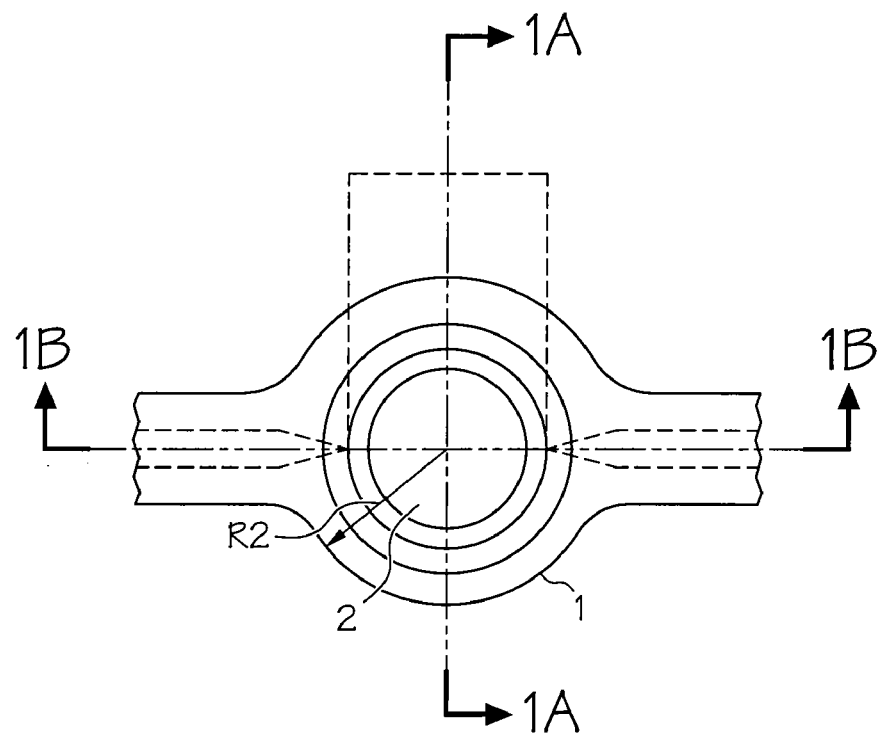
FIG. 1 is a top view onto a partial piece of one embodiment of a catheter in accordance with a first embodiment of the present invention, comprising a clip.

FIG. 1 shows a first embodiment of a blocking valve 2 which is formed on a catheter 1, directly on or in the flexible catheter tube and in the vicinity of the outlet point of a pump (not shown). The blocking valve 2 is configured such that it blocks or prevents flow when an interior pressure of the flexible tube or a pressure of the medium being guided in the flexible tube 1 is 0.1 bar or less, and opens at higher pressures and allows a flow through the flow region 1b of the catheter 1.

The first embodiment of the catheter 1 shown can, for example, be obtained by reshaping the catheter or flexible tube in the region of the valve 2 by a thermal reshaping method, wherein the annular or tubular cross-section of the catheter 1 is reshaped in the region of the valve 2 into a flat flexible tube, as shown in the sectional view in FIG. 1A, such that the wall halves 1a of the catheter 1 abut each other and can thus prevent a flow when a low interior pressure is being applied. If the pressure of the medium being guided in the catheter 1 rises above a predetermined minimum pressure of, for example 0.1 bar, the inner wall 1c of the catheter is pushed open and the valve 2 is opened, such that a flow through the catheter 1 is possible.

As can be seen from FIGS. 1A and 1B, the valve 2 can be fitted with a clip 3 which is formed as a U-shaped spring element and comprises pressing pieces 3a and 3b. The clip 3 is arranged around the catheter 1 and can bias the catheter halves and therefore the inner walls 1c of the catheter against each other via its clamping force. By using the clip 3, it is possible to set a defined blocking force or blocking pressure. The greater the force with which the clip 3 presses the catheter walls 1c onto each other, the greater the minimum pressure of the medium which has to be applied to enable a flow through the catheter 1.

If such a catheter 1, comprising one or more valves 2 successively arranged in the longitudinal direction of the catheter 1, is connected to an administering device, for example an infusion pump, the catheter 1 is connected to a reservoir 4 for a substance or medium to be administered. Usually, a stopper 5 is inserted into the reservoir 4 or an ampoule 4 by an infusion pump, such that the interior pressure in the ampoule 4 is increased and a substance contained in the ampoule 4 is dispensed from a dispensing opening 4a of the ampoule 4. This causes a rise in pressure in the connected catheter 1, which ensures that the catheter walls 1a, which are biased against each other, are pushed open and that a desired amount of the substance, such as for example insulin, can thus be dispensed to a patient. As soon as the desired amount of the substance has been administered, and the stopper 5 of the reservoir 4 is at rest again, the valve 2 closes due to the force of the clip 3 which presses the catheter 1 together again, automatically. The opening pressure for the valve 2 is thus set or defined by the biasing force of the clip 3.

Figure 2:
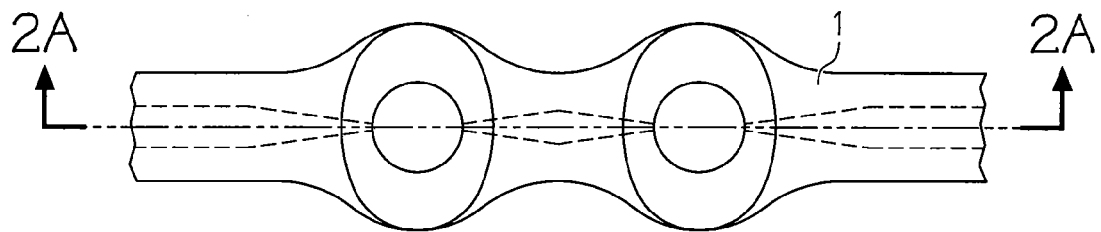
FIG. 2 depicts a second embodiment of a self-blocking catheter in accordance with the present invention comprising two blocking regions.
Figure 2A:
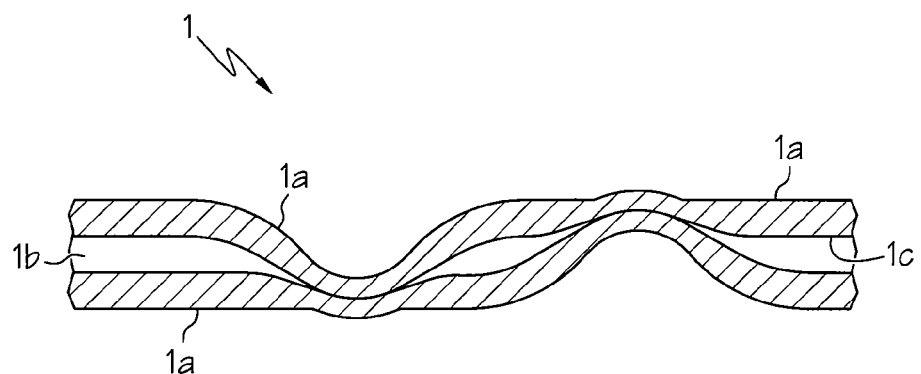
FIG. 2A is a cross-sectional view along the line A-A in FIG. 2.

FIG. 2 shows a second embodiment of a catheter 1 in accordance with the present invention, comprising two valves 2. The two valves 2 are arranged in two zones spaced apart from each other in the longitudinal direction of the catheter 1, i.e along the length of the catheter, and comprise catheter walls 1a which are respectively biased against each other, wherein one catheter wall 1a of a first side, shown on the left in FIG. 2A, is biased toward the second side (in the drawing, downwardly), such that the inner walls 1a of the catheter abut each other and prevent a flow of a medium when a predetermined minimum pressure is not being applied. In the region of the second valve, shown on the right, the bias relative to the first valve is reversed, i.e. the opposing second side is biased toward the first side, such that the desired valve blocking effect occurs.

Each bias of a catheter wall 1a can thus be regarded as an aperture. If a number of apertures are arranged in series, the overall difference in pressure is divided into stage differences in pressure, such that the drop in pressure per valve zone can be reduced. Reducing the overall difference in pressure is advantageous, since the closing force per valve zone can then be reduced and the functional reliability of the overall valve, formed from a number of valve zones, can thus be increased.

In accordance with another embodiment of the present invention, a valve function using a catheter 1 can be achieved by moving the catheter 1 into a sharply bent region using a defined path-force element (spring). When the pressure rises, for example between 0.5 and 0.8 bar, the catheter 1 is released from the sharply bent region and so releases the flow.

Figure 3:
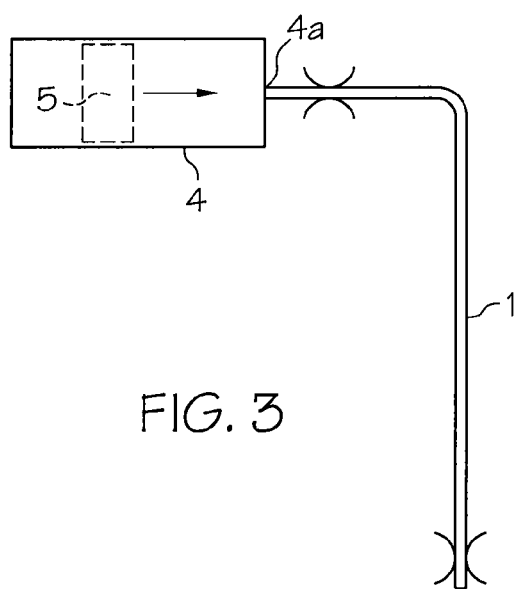
FIG. 3 is a schematic representation illustrate the working principle of one embodiment of the present invention.

FIG. 3 schematically shows an ampoule 4 comprising a stopper 5 which can be shifted within it in the direction of the arrow and using which a substance contained in the ampoule 4 can be dispensed from a dispensing opening 4a to the catheter 1 connected to the ampoule 4. If, for example, the difference in height between the lower and upper end of the catheter 1 measured one metre, then a partial vacuum of 0.1 bar would be applied at the upper end of the catheter 1, which could cause a substance to be unintentionally dispensed from the ampoule 4 in an uncontrolled manner, solely due to the hydrostatic pressure generated by the column of fluid in the catheter 1.

It is therefore advantageous, in some embodiments, to arrange a valve in the upper region of the catheter, since a partial vacuum of 0.1 bar in relation to a relative exterior pressure of 0 bar causes the catheter walls 1a to be automatically pressed together. If the catheter walls 1a are elastic, the partial vacuum in the upper catheter portion can therefore be utilized such that in the event of a hydrostatic pressure distribution in the catheter, the valve is automatically closed.

If the above-described catheter 1 in accordance with the present invention is used, then it is possible to prevent a substance from being unintentionally dispensed from the ampoule 4 through the catheter 1.

Figure 4:
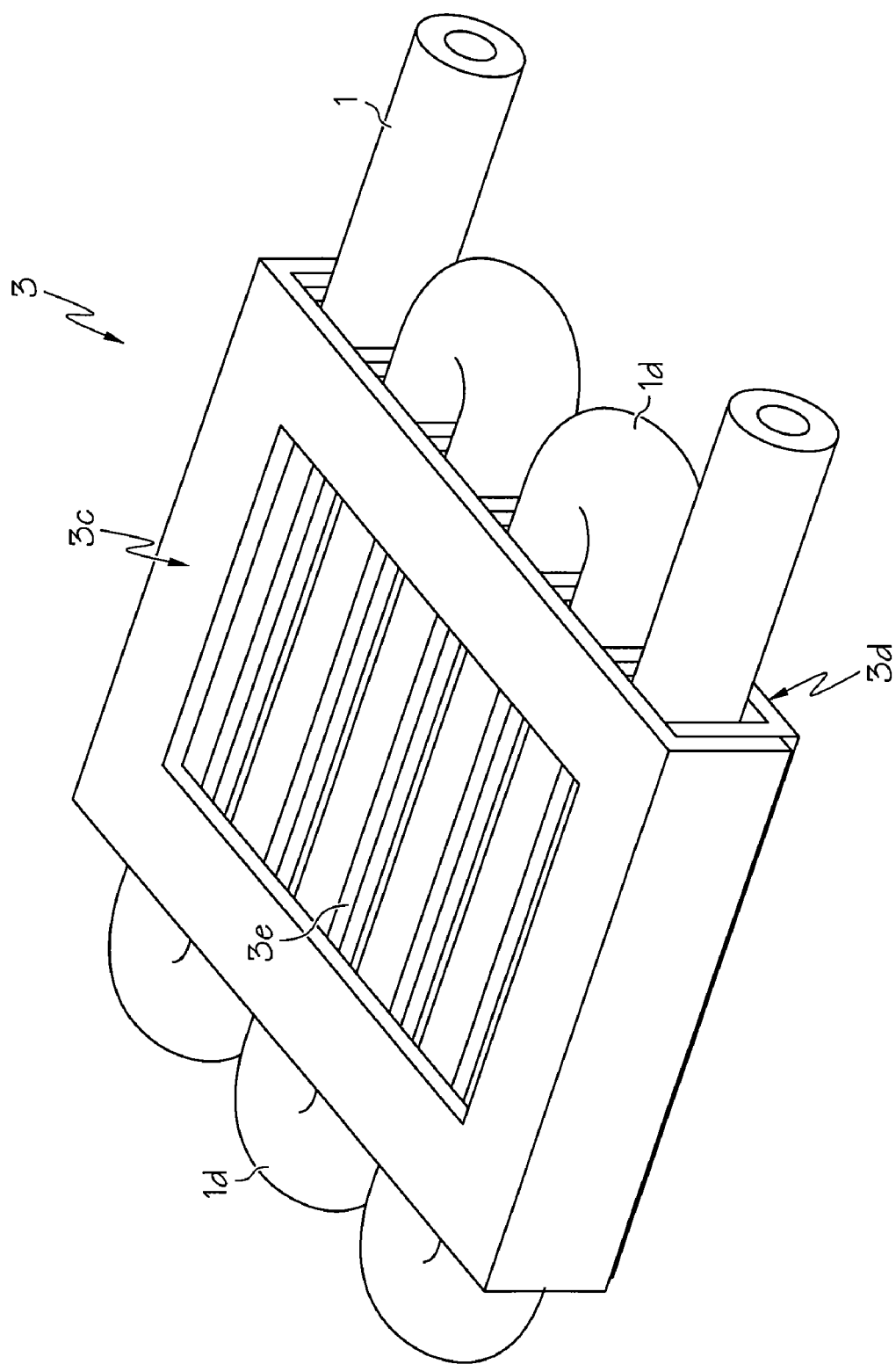
FIG. 4 depicts a third embodiment comprising a number of successively arranged, sharply bent regions.

In some embodiments, a number of sharply bent regions 1d can also be successively arranged, as shown in FIG. 4, wherein a catheter or flexible tube 1 is accommodated in a clamping piece or clip 3 which can consist of an upper part 3c of the clamping piece and a lower part 3d of the clamping piece, which can be connected to each other. The catheter 1 is inserted into the catheter guides, which are, for example, formed by a number of mutually parallel partition walls 3e, such that the catheter 1 is held meandering, or snaking or winding, in the clamping piece 3, wherein linear regions of the catheter 1 are parallel to each other, separated by the wall pieces 3e, wherein a sharply bent region 1d is provided in each region in which the catheter 1 transitions from one guide, formed by two adjacent wall pieces 3e, to the next guide. FIG. 4 shows the open-catheter state, in which the sharply bent regions 1d are open, due to an applied pressure of, for example, more than 0.7 bar, and so enable a flow of a medium through the catheter 1. If a pressure below 0.7 bar is being applied, the catheter 1 is deformed in the region of the sharp bends 1d, such that a medium is prevented from passing through the catheter 1.

The clamping piece 3 can, for example, be formed to be rigid, such that when the pressure of the medium being guided in the catheter 1 rises above 0.7 bar, a flow is enabled solely by the deformation of the catheter 1. Alternatively, the clamping piece 3 can also be formed to be elastic or flexible, such that when the pressure of the medium being guided in the catheter 1 rises, the clamping piece 3 is deformed or expanded and so releases the flow for the fluid being guided in the catheter 1.

Although the clamping piece 3 could in principle be formed in one piece, in some preferred embodiments it is formed—to more easily insert the catheter 1—from two partial pieces 3c and 3d which can be placed onto each other or connected to each other, after the catheter 1 has been inserted into the clamping piece 3d in the manner shown in FIG. 4, such that the catheter 1 exhibits a number of successive sharply bent regions 1d on two opposing sides of the clamping piece 3.

Figure 5A:
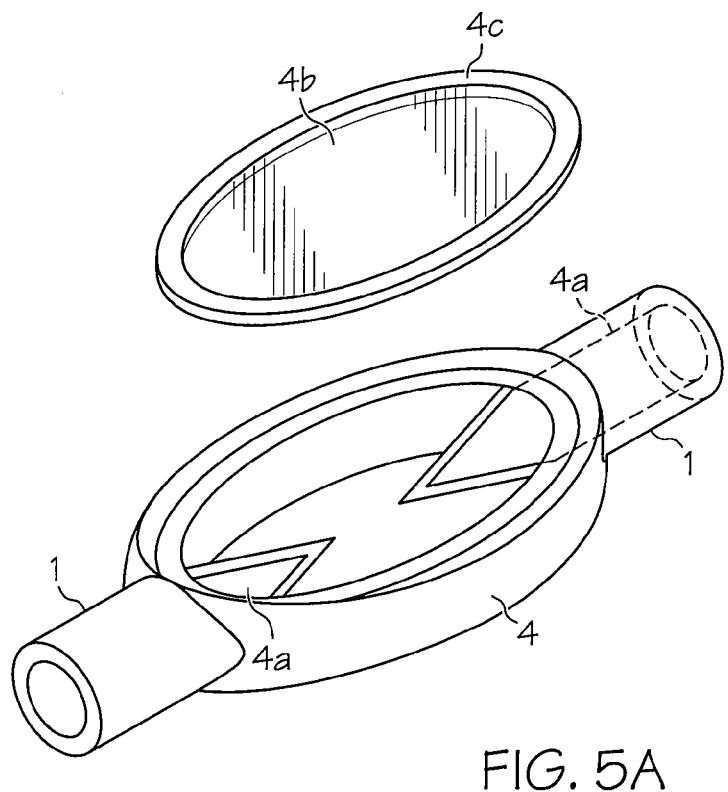
FIGS. 5A, 5B, and 5C depict another embodiment of a self-blocking catheter in accordance with the present invention comprising a separate pressure element.

FIG. 5A shows another embodiment of a blocking mechanism for a catheter 1, wherein a catheter blocking valve can be both integrated into the catheter 1 and formed as a separate valve piece which can be inserted between two catheter pieces 1. In the embodiment shown in FIG. 5A, a valve base body 4 made from a thermoplastic elastomer (TPE) can be seen which is formed in the shape of a disc or plate and is flat. The body 4 has been inserted between two catheter pieces 1, wherein the body 4 has been placed onto the catheter pieces 1 in the region of a fusing zone 4a and connected or fused to the catheter pieces 1, so as to be an integrated part of the catheter. A sealing or covering element 4b, in the form of a film which is likewise formed from a thermoplastic elastomer, is placed onto the valve base body 4 and can be formed double-layered and from a different material than the valve base body 4. The film 4b is connected to the valve base body 4 in the region of a fusing zone 4c.

Figure 5B:
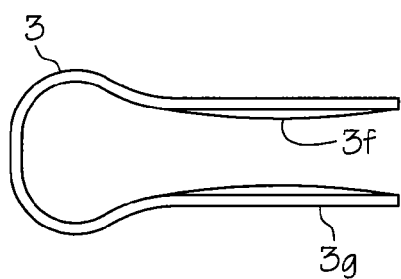
Figure 5C:
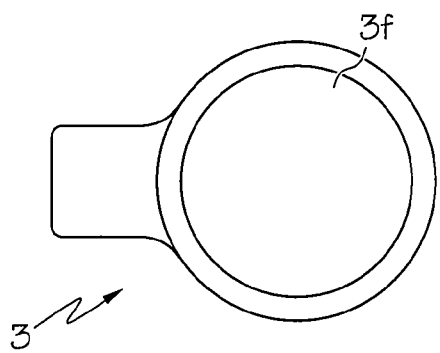

A bent clip 3 formed from spring steel may be slid or placed onto the valve base body 4 connected to the film 4b, in a similar way to the embodiment described with respect to FIG. 1. The clip comprises two mutually opposing pressure surfaces 3f and 3g, such that the upper pressure surface 3f can press onto the film 4b and the lower surface 3g can press onto the lower side of the valve base body 4. FIG. 5C is a top view onto the clip 3 which is shown in a lateral view in FIG. 5B.

If a pressure of, for example, less than 0.7 bar is being applied to the medium being transported in the catheter 1, then the film 4b is pressed into the valve base body 4 or the valve base body 4 is pressed together with the film 4b, such that a flow of a medium cannot occur. If the pressure of the medium rises above 0.7 bar, then the clip 3 is pressed or urged apart by the pressure of the medium, i.e. the pressure surfaces 3f and 3g are urged away from each other enabling a flow of the medium.

The blocking pressure of the valve shown in FIG. 5 can be altered by the configuration of the clip 3, and/or by its manufacture, deformation and material constants or processing, such that the valve can also open at a lower pressure of, for example, 0.1 bar or 0.2 bar or at a higher pressure of, for example, 1 bar or above.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for preventing free flow through a catheter for connecting an administering device to an administering needle comprising:
   the catheter comprising a catheter wall, and a flow region defined by the catheter wall, the catheter having a number of linear sections and intermediate sections connecting a distal end of one linear section with a proximal end of the next linear section; and
   a clip comprising an upper part and a lower part, the catheter arranged in the clip so that adjacent linear sections of the catheter are parallel to each other, and the intermediate section connecting one linear section to the next linear section is sharply bent, and wherein in the sharply bent intermediate sections, at least one partial piece of an inner wall abuts at least one other partial piece of the inner wall to block a flow of a medium through the catheter, wherein the partial pieces are separated when the medium exhibits a pressure above a predetermined blocking pressure, thereby permitting the flow.

2. The device of claim 1 wherein the clip includes parallel partition walls and wherein the linear sections of the catheter are arranged between the parallel partition walls.

3. The catheter according to claim 1, wherein the blocking pressure is around at least 0.1 bar or above.

4. The catheter according to claim 3, wherein the blocking pressure is one of approximately 0.2 bar, approximately 0.3 bar or approximately 0.7 bar.

5. A system comprising:
an administering device; and
a catheter for connecting the administering device to a needle, the catheter comprising a catheter wall and a flow region defined by the catheter wall, the catheter having a number of linear sections and intermediate sections connecting a distal end of one linear section with a proximal end of the next linear section; and
a clip comprising an upper part and a lower part, the catheter arranged in the clip so that adjacent linear sections of the catheter are parallel to each other, and the intermediate section connecting one linear section to the next linear section is sharply bent, and wherein in the sharply bent intermediate sections, at least one partial piece of an inner wall abuts at least one other partial piece of the inner wall to block a flow of a medium through the catheter, wherein the partial pieces are separated when the medium exhibits a pressure above a predetermined blocking pressure, thereby permitting the flow.

6. The system of claim 5 wherein the clip includes parallel partition walls and wherein the linear sections of the catheter are arranged between the parallel partition walls.

7. The system according to claim 5, wherein the blocking pressure is around at least 0.1 bar or above.

8. The system according to claim 7, wherein the blocking pressure is one of approximately 0.2 bar, approximately 0.3 bar or approximately 0.7 bar.

9. The system according to claim 5, wherein the administering device is an infusion pump.

10. The system according to claim 9, wherein the catheter has two ends and wherein one of the needle or an infusion set is connected to the end of the catheter opposite the end of the catheter connected to the infusion pump.

11. The system according to claim 10, wherein the clip is near the infusion pump.

12. A method for controlling a flow of a medium through a catheter, the method comprising the steps of:
providing the catheter comprising a catheter wall, and a flow region defined by the catheter wall, the catheter having a number of linear sections and intermediate sections connecting a distal end of one linear section with a proximal end of the next linear section; and a clip comprising an upper part and a lower part, the catheter arranged in the clip so that adjacent linear sections of the catheter are parallel to each other, and the intermediate section connecting one linear section to the next linear section is sharply bent, and wherein in the sharply bent intermediate sections, at least one partial piece of an inner wall abutting at least one other partial piece of the inner wall to block a flow of a medium through the catheter below a predetermined minimum pressure of the medium to prevent the flow of the medium through the catheter, and
exceeding the minimum pressure to separate the partial pieces in the sharply bent regions sections to enable the flow.

13. The method of claim 12 wherein the clip includes parallel partition walls and wherein the linear sections of the catheter are arranged between the parallel partition walls.

14. The method according to claim 12, wherein the blocking pressure is around at least 0.1 bar or above.

15. The method according to claim 14, wherein the blocking pressure is one of approximately 0.2 bar, approximately 0.3 bar or approximately 0.7 bar.

16. The method according to claim 12, further comprising providing an administering device connected to the catheter.

17. The method according to claim 16 wherein the administering device is an infusion pump.

18. The method according to claim 16, wherein the catheter has two ends and wherein one of a needle or an infusion set is connected to the end of the catheter opposite the end of the catheter connected to the administering device.

19. The method according to claim 18, wherein the clip is near the administering device.

* * * * *

UNITED STATES PATENT AND TRADEMARK OFFICE
CERTIFICATE OF CORRECTION

| | | |
|---|---|---|
| PATENT NO. | : 8,114,056 B2 | Page 1 of 1 |
| APPLICATION NO. | : 12/644446 | |
| DATED | : February 14, 2012 | |
| INVENTOR(S) | : Hanspeter Niklaus et al. | |

It is certified that error appears in the above-identified patent and that said Letters Patent is hereby corrected as shown below:

Col. 1, Line 59, "known systems involving" should read --known systems involve--

Col. 5, Line 34, "illustrate" should read --illustrating--

Col. 10, Claim 10, Line 2, "one of the needle" should read --one of the needles--

Col. 10, Claim 12, Line 26, "sharply bent regions sections" should read --sharply bent section--

Signed and Sealed this
Twenty-eighth Day of August, 2012

David J. Kappos
*Director of the United States Patent and Trademark Office*